(12) United States Patent
Long et al.

(10) Patent No.: US 7,419,664 B2
(45) Date of Patent: Sep. 2, 2008

(54) METHOD OF TREATMENT USING ANTIBODY TO CLCA-1

(75) Inventors: Andrew J. Long, Chelmsford, MA (US); Clive R. Wood, Boston, MA (US); Michael Bowman, Westwood, MA (US); Samuel J. Goldman, Acton, MA (US); Joseph P. Sypek, Woburn, MA (US)

(73) Assignee: Wyeth, Madison, NJ (US)

( * ) Notice: Subject to any disclaimer, the term of this patent is extended or adjusted under 35 U.S.C. 154(b) by 526 days.

(21) Appl. No.: 10/855,745

(22) Filed: May 27, 2004

(65) Prior Publication Data

US 2004/0265314 A1 Dec. 30, 2004

Related U.S. Application Data

(60) Provisional application No. 60/474,174, filed on May 28, 2003.

(51) Int. Cl.
*A61K 39/395* (2006.01)
(52) U.S. Cl. .................................. 424/139.1
(58) Field of Classification Search ........................ None
See application file for complete search history.

(56) References Cited

U.S. PATENT DOCUMENTS 6,716,603 B2 * 4/2004 Holroyd et al. ............ 435/69.1

FOREIGN PATENT DOCUMENTS

EP        1 234 878 A1    8/2002
WO       WO 99/44620      9/1999
WO       WO 01/54685      8/2001

OTHER PUBLICATIONS

Clarke et al., "Defective epithelial chloride transport in a gene-targeted mouse model of cystic fibrosis," *Science*, 257:1125-1128 (1992).
Clarke et al., "Relationship of a non-cystic fibrosis transmembrane conductance regulator-mediated chloride conductance to organ-level disease in *Cftr(-/-)* mice," *PNAS*, 91:479-483 (1994).
Eng et al., "Short-term efficacy of ultrasonically nebulized hypertonic saline in cystic fibrosis," *Ped. Pulmonol.*, 21:77-83 (1996).
Gruber et al., "Genomic cloning, molecular characterization, and functional analysis of human CLCA1, the first human member of the family of $Ca^{2+}$-activated $Cl^-$ channel proteins," *Genomics*, 54:200-214 (1998).
Hoshino et al., "Increased expression of the human $Ca^{2+}$-activated $Cl^-$ channel 1 (CaCC1) gene in the asthmstic airway," *Am. J. Respir. Crit. Care Med.*, 165:1132-1136 (2002).
Nakanishi et al., "Role of gob-5 in mucus overproduction and airway hyperresponsiveness in asthma," *PNAS*, 98:5175-5180 (2001).
Welsh et al., "Molecular mechanisms of CFTR chloride channel dysfunction in cystic fibrosis," *Cell*, 73:1251-1254 (1993).
International Search Report for PCT/US2004/016742 dated Dec. 28, 2004.

* cited by examiner

*Primary Examiner*—Michael Pak
(74) *Attorney, Agent, or Firm*—Finnegan, Henderson, Farabow, Garrett & Dunner, L.L.P.

(57) ABSTRACT

The invention relates to methods of treating a disease or condition, wherein expression or activity of soluble CLCA1 is up-regulated, by administering inhibitors of soluble CLCA1. The invention also relates to methods of isolating soluble CLCA1 from a bodily fluid.

4 Claims, 14 Drawing Sheets

Figure 1

```
MGPFKSSVFI  LILHLLEGAL  SNSLIQLNNN  GYEGIVVAID
PNVPEDETLI  QQIKDMVTQA  SLYLFEATGK  RFYFKNVAIL
IPETWKTKAD  YVRPKLETYK  NADVLVAEST  PPGNDEPYTE
QMGNCGEKGE  RIHLTPDFIA  GKKLAEYGPQ  GRAFVHEWAH
LRWGVFDEYN  NDEKFYLSNG  RIQAVRCSAG  ITGTNVVKKC
QGGSCYTKRC  TFNKVTGLYE  KGCEFVLQSR  QTEKASIMFA
QHVDSIVEFC  TEQNHNKEAP  NKQNQKCNLR  STWEVIRDSE
DFKKTTPMTT  QPPNPTFSLL  QIGQRIVCLV  LDKSGSMATG
NRLNRLNQAG  QLFLLQTVEL  GSWVGMVTFD  SAAHVQSELI
QINSGSDRDT  LAKRLPAAAS  GGTSICSGLR  SAFTVIRKKY
PTDGSEIVLL  TDGEDNTISG  CFNEVKQSGA  IIHTVALGPS
AAQELEELSK  MTGGLQTYAS  DQVQNNGLID  AFGALSSGNG
AVSQRSIQLE  SKGLTLQNSQ  WMNGTVIVDS  TVGKDTLFLI
TWTTQPPQIL  LWDPSGQKQG  GFVVDKNTKM  AYLQIPGIAK
VGTWKYSLQA  SSQTLTLTVT  SRASNATLPP  ITVTSKTNKD
TSKFPSPLVV  YANIRQGASP  ILRASVTALI  ESVNGKTVTL
ELLDNGAGAD  ATKDDGVYSR  YFTTYDTNGR  YSVKVRALGG
VNAARRRVIP  QQSGALYIPG  WIENDEIQWN  PPRPEINKDD
VQHKQVCFSR  TSSGGSFVAS  DVPNAPIPDL  FPPGQITDLK
AEIHGGSLIN  LTWTAPGDDY  DHGTAHKYII  RISTSILDLR
DKFNESLQVN  TTALIPKEAN  SEEVFLFKPE  NITFENGTDL
FIAIQAVDKV  DLKSEISNIA  RVSLFIPPQT  PPETPSPDET
SAPCPNIHIN  STIPGIHILK  IMWKWIGELQ  LSIA
```

Figure 4
Serum Albumin
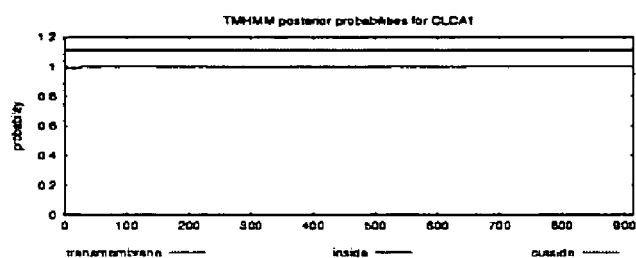
CLCA
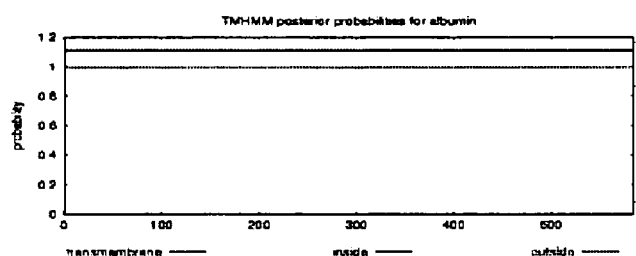
CFTR
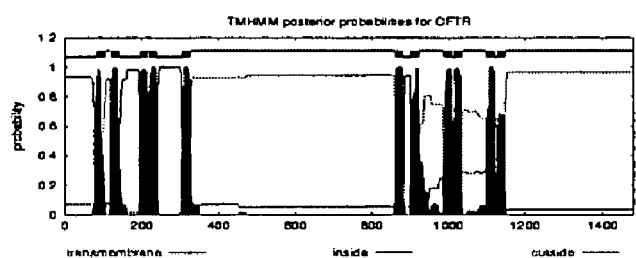
ClC
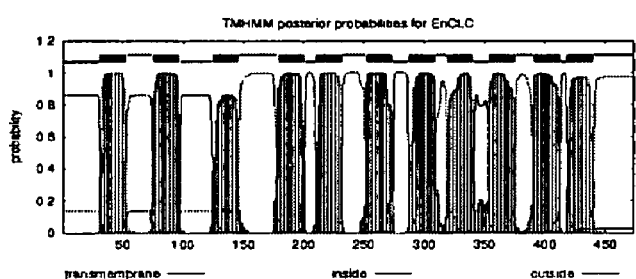

Figure 5
Serum Albumin
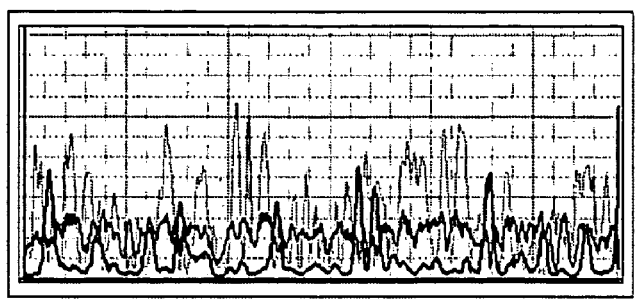
CLCA
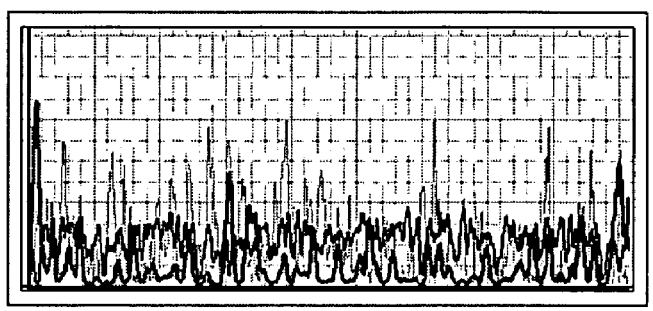
CFTR
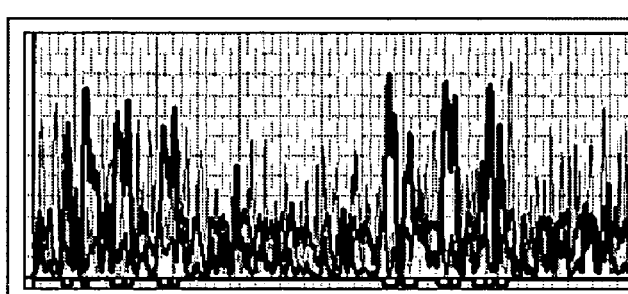
CIC
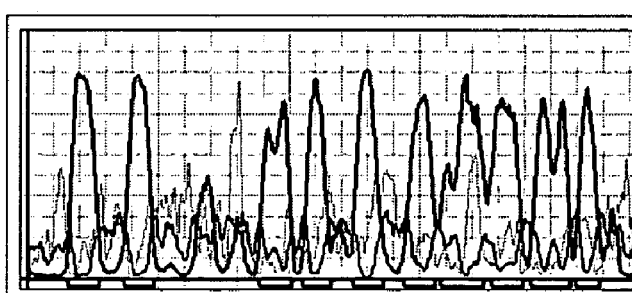

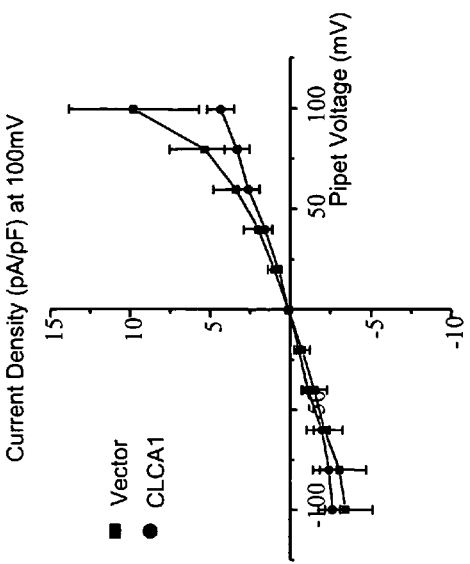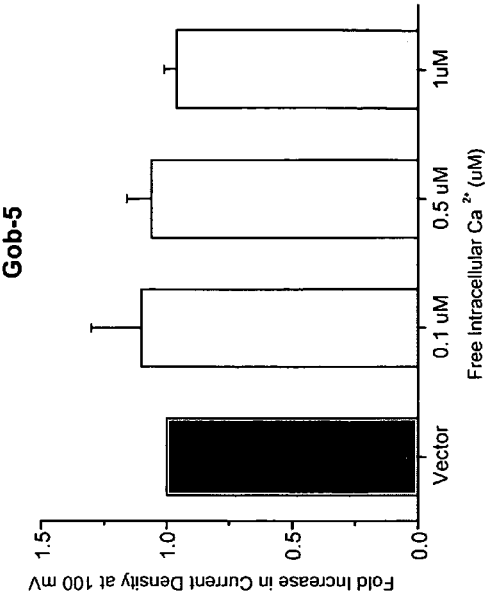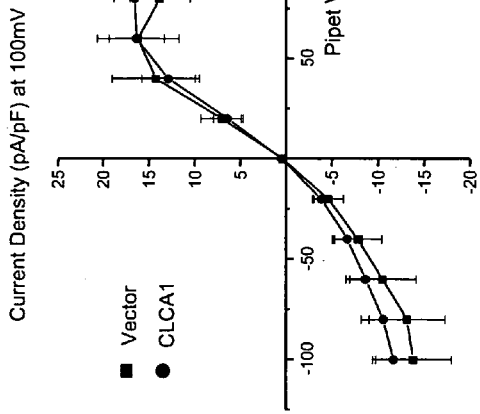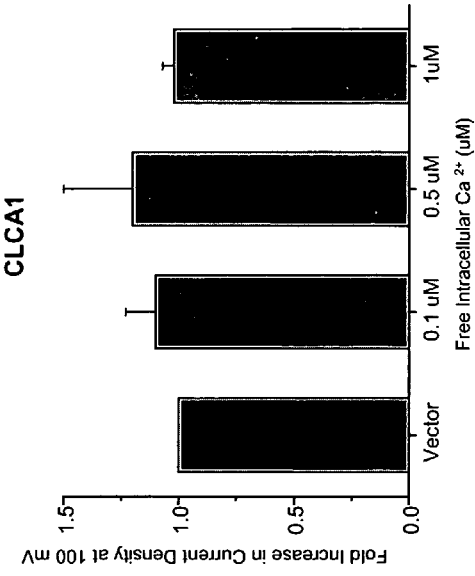
Fig 13

SEQUENCE LISTING

<160> NUMBER OF SEQ ID NOS: 10

<210> SEQ ID NO 1
<211> LENGTH: 39
<212> TYPE: DNA

<210> ORGANISM: Homo sapiens

<400> SEQUENCE: 1
cgcaagcttg ggatggggcc atttaagagt tctgtgttc        39

<210> SEQ ID NO 2
<211> LENGTH: 39
<212> TYPE: DNA
<213> ORGANISM: Homo sapiens

<400> SEQUENCE: 2
cccaagcttt cactacttat taatttcagg tcttggtgg        39

<210> SEQ ID NO 3
<211> LENGTH: 41
<212> TYPE: DNA
<213> ORGANISM: Homo sapiens

<400> SEQUENCE: 3
cccaagcttt cactaccttg agtagacacc gtcatcctta g        41

<210> SEQ ID NO 4
<211> LENGTH: 48
<212> TYPE: DNA
<213> ORGANISM: Homo sapiens

<400> SEQUENCE: 4
cccaagcttt cactattgat ctgaagcata tgtctgtaaa cctccctg        48

<210> SEQ ID NO 5
<211> LENGTH: 15
<212> TYPE: PRT
<213> ORGANISM: Homo sapiens

<400> SEQUENCE: 5

Gly Glu Lys Gly Glu Arg Ile His Leu Thr Pro Asp Phe Ile Ala
1               5                   10                  15

<210> SEQ ID NO 6
<211> LENGTH: 15
<212> TYPE: PRT
<213> ORGANISM: Homo sapiens

<400> SEQUENCE: 6

Glu Gln Asn His Asn Lys Glu Ala Pro Gln Lys Gln Asn Gln Lys
1               5                   10                  15

<210> SEQ ID NO 7
<211> LENGTH: 17
<212> TYPE: PRT
<213> ORGANISM: Homo sapiens

<400> SEQUENCE: 7

Gly Gln Gly Val Ser Gln Arg Ser Ile Gln Leu Glu Ser Lys Gly Leu
1               5                   10                  15

Thr

<210> SEQ ID NO 8
<211> LENGTH: 15
<212> TYPE: PRT
<213> ORGANISM: Homo sapiens

<400> SEQUENCE: 8

```
Ile Glu Asn Asp Glu Ile Gln Trp Asn Pro Pro Arg Pro Glu Ile
1               5                   10                  15
```

<210> SEQ ID NO 9
<211> LENGTH: 15
<212> TYPE: PRT
<213> ORGANISM: Homo sapiens

<400> SEQUENCE: 9

```
Lys Glu Ala Asn Ser Glu Val Phe Leu Phe Lys Pro Glu Asn
1               5                   10                  15
```

<210> SEQ ID NO 10
<211> LENGTH: 914
<212> TYPE: PRT
<213> ORGANISM: Homo sapiens

<400> SEQUENCE: 10

```
Met Gly Pro Phe Lys Ser Ser Val Phe Ile Leu Ile Leu His Leu Leu
1               5                   10                  15

Glu Gly Ala Leu Ser Asn Ser Leu Ile Gln Leu Asn Asn Gly Tyr
                20                  25                  30

Glu Gly Ile Val Val Ala Ile Asp Pro Asn Val Pro Glu Asp Glu Thr
            35                  40                  45

Leu Ile Gln Gln Ile Lys Asp Met Val Thr Gln Ala Ser Leu Tyr Leu
    50                  55                  60

Phe Glu Ala Thr Gly Lys Arg Phe Tyr Phe Lys Asn Val Ala Ile Leu
65                  70                  75                  80

Ile Pro Glu Thr Trp Lys Thr Lys Ala Asp Tyr Val Arg Pro Lys Leu
                85                  90                  95

Glu Thr Tyr Lys Asn Ala Asp Val Leu Val Ala Glu Ser Thr Pro Pro
            100                 105                 110

Gly Asn Asp Glu Pro Tyr Thr Glu Gln Met Gly Asn Cys Gly Glu Lys
    115                 120                 125

Gly Glu Arg Ile His Leu Thr Pro Asp Phe Ile Ala Gly Lys Lys Leu
130                 135                 140

Ala Glu Tyr Gly Pro Gln Gly Arg Ala Phe Val His Glu Trp Ala His
145                 150                 155                 160

Leu Arg Trp Gly Val Phe Asp Glu Tyr Asn Asn Asp Glu Lys Phe Tyr
                165                 170                 175

Leu Ser Asn Gly Arg Ile Gln Ala Val Arg Cys Ser Ala Gly Ile Thr
            180                 185                 190

Gly Thr Asn Val Val Lys Lys Cys Gln Gly Gly Ser Cys Tyr Thr Lys
    195                 200                 205

Arg Cys Thr Phe Asn Lys Val Thr Gly Leu Tyr Glu Lys Gly Cys Glu
210                 215                 220

Phe Val Leu Gln Ser Arg Gln Thr Glu Lys Ala Ser Ile Met Phe Ala
225                 230                 235                 240

Gln His Val Asp Ser Ile Val Glu Phe Cys Thr Glu Gln Asn His Asn
                245                 250                 255

Lys Glu Ala Pro Asn Lys Gln Asn Gln Lys Cys Asn Leu Arg Ser Thr
            260                 265                 270

Trp Glu Val Ile Arg Asp Ser Glu Asp Phe Lys Lys Thr Thr Pro Met
    275                 280                 285

Thr Thr Gln Pro Pro Asn Pro Thr Phe Ser Leu Leu Gln Ile Gly Gln
290                 295                 300
```

-continued

```
Arg Ile Val Cys Leu Val Leu Asp Lys Ser Gly Ser Met Ala Thr Gly
305                 310                 315                 320

Asn Arg Leu Asn Arg Leu Asn Gln Ala Gly Gln Leu Phe Leu Leu Gln
                325                 330                 335

Thr Val Glu Leu Gly Ser Trp Val Gly Met Val Thr Phe Asp Ser Ala
            340                 345                 350

Ala His Val Gln Ser Glu Leu Ile Gln Ile Asn Ser Gly Ser Asp Arg
        355                 360                 365

Asp Thr Leu Ala Lys Arg Leu Pro Ala Ala Ser Gly Gly Thr Ser
    370                 375                 380

Ile Cys Ser Gly Leu Arg Ser Ala Phe Thr Val Ile Arg Lys Lys Tyr
385                 390                 395                 400

Pro Thr Asp Gly Ser Glu Ile Val Leu Leu Thr Asp Gly Glu Asp Asn
                405                 410                 415

Thr Ile Ser Gly Cys Phe Asn Glu Val Lys Gln Ser Gly Ala Ile Ile
                420                 425                 430

His Thr Val Ala Leu Gly Pro Ser Ala Gln Glu Leu Glu Glu Leu
        435                 440                 445

Ser Lys Met Thr Gly Gly Leu Gln Thr Tyr Ala Ser Asp Gln Val Gln
450                 455                 460

Asn Asn Gly Leu Ile Asp Ala Phe Gly Ala Leu Ser Ser Gly Asn Gly
465                 470                 475                 480

Ala Val Ser Gln Arg Ser Ile Gln Leu Glu Ser Lys Gly Leu Thr Leu
                485                 490                 495

Gln Asn Ser Gln Trp Met Asn Gly Thr Val Ile Val Asp Ser Thr Val
                500                 505                 510

Gly Lys Asp Thr Leu Phe Leu Ile Thr Trp Thr Thr Gln Pro Pro Gln
            515                 520                 525

Ile Leu Leu Trp Asp Pro Ser Gly Gln Lys Gln Gly Gly Phe Val Val
        530                 535                 540

Asp Lys Asn Thr Lys Met Ala Tyr Leu Gln Ile Pro Gly Ile Ala Lys
545                 550                 555                 560

Val Gly Thr Trp Lys Tyr Ser Leu Gln Ala Ser Ser Gln Thr Leu Thr
                565                 570                 575

Leu Thr Val Thr Ser Arg Ala Ser Asn Ala Thr Leu Pro Pro Ile Thr
            580                 585                 590

Val Thr Ser Lys Thr Asn Lys Asp Thr Ser Lys Phe Pro Ser Pro Leu
        595                 600                 605

Val Val Tyr Ala Asn Ile Arg Gln Gly Ala Ser Pro Ile Leu Arg Ala
610                 615                 620

Ser Val Thr Ala Leu Ile Glu Ser Val Asn Gly Lys Thr Val Thr Leu
625                 630                 635                 640

Glu Leu Leu Asp Asn Gly Ala Gly Ala Asp Ala Thr Lys Asp Asp Gly
                645                 650                 655

Val Tyr Ser Arg Tyr Phe Thr Thr Tyr Asp Thr Asn Gly Arg Tyr Ser
            660                 665                 670

Val Lys Val Arg Ala Leu Gly Gly Val Asn Ala Ala Arg Arg Val
        675                 680                 685

Ile Pro Gln Gln Ser Gly Ala Leu Tyr Ile Pro Gly Trp Ile Glu Asn
        690                 695                 700

Asp Glu Ile Gln Trp Asn Pro Arg Pro Glu Ile Asn Lys Asp Asp
705                 710                 715                 720

Val Gln His Lys Gln Val Cys Phe Ser Arg Thr Ser Ser Gly Gly Ser
```

```
                        725                 730                 735
Phe Val Ala Ser Asp Val Pro Asn Ala Pro Ile Pro Asp Leu Phe Pro
                740                 745                 750

Pro Gly Gln Ile Thr Asp Leu Lys Ala Glu Ile His Gly Gly Ser Leu
            755                 760                 765

Ile Asn Leu Thr Trp Thr Ala Pro Gly Asp Asp Tyr Asp His Gly Thr
        770                 775                 780

Ala His Lys Tyr Ile Ile Arg Ile Ser Thr Ser Ile Leu Asp Leu Arg
785                 790                 795                 800

Asp Lys Phe Asn Glu Ser Leu Gln Val Asn Thr Thr Ala Leu Ile Pro
                805                 810                 815

Lys Glu Ala Asn Ser Glu Glu Val Phe Leu Phe Lys Pro Glu Asn Ile
            820                 825                 830

Thr Phe Glu Asn Gly Thr Asp Leu Phe Ile Ala Ile Gln Ala Val Asp
        835                 840                 845

Lys Val Asp Leu Lys Ser Glu Ile Ser Asn Ile Ala Arg Val Ser Leu
    850                 855                 860

Phe Ile Pro Pro Gln Thr Pro Pro Glu Thr Pro Ser Pro Asp Glu Thr
865                 870                 875                 880

Ser Ala Pro Cys Pro Asn Ile His Ile Asn Ser Thr Ile Pro Gly Ile
                885                 890                 895

His Ile Leu Lys Ile Met Trp Lys Trp Ile Gly Glu Leu Gln Leu Ser
            900                 905                 910

Ile Ala
```

METHOD OF TREATMENT USING ANTIBODY TO CLCA-1

This application claims priority to U.S. Provisional Application No. 60/474,174 filed May 28, 2003.

FIELD OF THE INVENTION

The invention relates to soluble Calcium Activated Chloride Channel 1 (CLCA1) and antagonists which inhibit the activity of soluble CLCA1. The invention relates in part to methods of isolating and using soluble CLCA1 and antagonists to soluble CLCA1 to treat diseases and conditions associated with the abnormal activity of CLCA1.

BACKGROUND OF THE INVENTION

Ion transport across the plasma membrane is critical for maintaining the normal physiology of the cell. Ion transport across the plasma membrane is mediated by a variety of membrane bound proteins which act as channels and pumps. Dysfunctional ion channels or pumps will lead to a disease state. Cystic fibrosis is a disease resulting from a defect in a cAMP-mediated chloride channel, CFTR (Welsh et al. 1993, *Cell* 73:1251). The physiological manifestation of cystic fibrosis includes airway obstruction resulting from thick secretions of mucus into the airways of the lung and gastrointestinal tract and the subsequent colonization of the lung airways by pathogenic microorganisms (Clarke et al. 1992, *Science* 257:1125; Clarke et al. 1994, *Proc Natl Acad Sci USA* 91:479; Eng et al. 1996, *Ped Pulmonol* 21:77) and mucus plugging of pancreatic ducts of the gastrointestinal tract (WO 01/54685). The association of cystic fibrosis with aberrant ion transport has lead investigators to hypothesize that dysfunctional ion transport might be related to other diseases with similar symptoms. Thus, dysfunctional ion transport has been implicated in diseases such as asthma and chronic obstructive pathway disease (COPD), i.e., emphysema and chronic bronchitis.

CLCA1, and its murine homolog, gob-5, are putative calcium activated chloride channels (WO 99/44620). Both have been implicated in the pathology associated with asthma. Asthma is characterized by a hypersensitivity to environmental allergens which is associated with an inflammatory response and the increased production of mucin (WO 01/54685; WO 99/44620). Expression of CLCA1 and gob-5 are up-regulated in response to allergen challenge. Expression has also been linked to mucin overproduction (Hoshino et al. 2002, *Am J Respir Crit Care Med* 165:1132). Over expression of CLCA1 and gob-5 has been shown to induce expression of MUC5AC, a mucin gene, in a muco-epidermal cell line. Additionally, adenovirus mediated antisense therapy has abrogated the effects of gob-5 hyper-responsiveness and mucin production in an in vivo mouse model (Nakanishi et al. 2001, *Proc Natl Acad Sci USA* 98:5175).

It has been suggested that CLCA1 is expressed as a 125 kD precursor which is cleaved to form a 90 kD subunit and a 37 kD subunit which associate on the cell surface to form an active ion channel. It has also been suggested that the 90 kD subunit forms four transmembrane domains. It has further been suggested that expression of CLCA1 is associated with chloride ion flux across the plasma membrane and that non-selective chloride channel inhibitors such as niflumic acid, 4,4'-diisothiocyanatostilbene-2,2'-disulfonic acid, and dithiothreitol will abrogate this effect. (Gruber et al. 1999, *Genomics* 54:200).

SUMMARY OF THE INVENTION

The present invention is based at least in part on the discovery that CLCA1 is a secreted protein that can interact, e.g., associate with an extra-cellular molecule, e.g., a cell membrane or a cell membrane associated molecule. Because CLCA1 is a secreted protein it provides a convenient target for treating diseases associated with the increased expression or activity of CLCA1, e.g., atopic diseases such as asthma or COPD-like diseases which are characterized by high levels of mucin.

The invention relates to a method of treating a subject having a disease or condition wherein CLCA1 expression or activity is elevated in the subject compared to an individual without the disease or condition, said method comprising administering to said subject a therapeutically effective amount of at least one agent which inhibits or prevents an interaction or association of soluble CLCA1 with an extra-cellular molecule, e.g., association with a cell membrane molecule, thereby treating the disease or condition. Therefore, the invention provides for new methods of treating atopic diseases or conditions such as asthma or diseases such as COPD.

The invention relates to a method of modulating CLCA1 expression or activity in a cell, e.g. reducing CLCA1 expression or activity, said method comprising administering an effective amount of at least one agent which inhibits or prevents an interaction or association of soluble CLCA1 with an extra-cellular molecule, e.g., association with a cell membrane molecule, thereby reducing the expression or activity of CLCA1.

The agent can be an antibody or antigen binding fragment thereof which binds to CLCA1; a small molecule; a peptide or a peptide mimetic.

The invention further relates to a method of isolating CLCA1 comprising obtaining a fluid from a subject; contacting said fluid with a specific binding partner of CLCA1 such that a complex between CLCA1 and the specific binding partner forms; isolating the complex of CLCA1 and the specific binding partner of CLCA1; and disrupting the complex of CLCA1 and the specific binding partner of CLCA1 such that CLCA1 is isolated.

Additional objects and advantages of the invention will be set forth in part in the description which follows, and in part will be obvious from the description, or may be learned by practice of the invention. The objects and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1 depicts the primary amino acid sequence of human CLCA1. The VWA domain is underlined and the putative N-linked glycosylation sites are marked with an asterisk. The signal sequence is indicated by SS (SEQ ID NO: 10).

FIG. 4 depicts a hydrophobicity analysis of CLCA1 compared to other known membrane bound and secreted proteins using the computer program TMHMM. CLCA1 does not contain any membrane-spanning alpha helices.

FIG. 5 depicts a hydrophobicity analysis of CLCA1 compared to other known membrane bound and secreted proteins using the computer program Split 4.0. CLCA1 does not contain any membrane-spanning alpha helices.

FIG. 13 shows whole-cell patch clamp recording of transiently expressed CLCA1 and gob-5 in HEK 293 and A549 cells. FIG. 13(a) shows current-voltage relationship of transiently expressed CLCA1 in HEK 293 cells (left panel) and in A549 cells (right panel) at 0.5 M free Ca2+ in the pipette solution (n=6-8 in each group). FIG. 13(b) shows calcium-dependent fold increase in whole-cell current density in HEK 293 cells, transiently expressing hCLCA1 (left panel) and gob-5 (right panel) (n=3-8 in each group). Similar data was also observed in A549 (data not shown).

DESCRIPTION OF THE EMBODIMENTS

Figure 2:
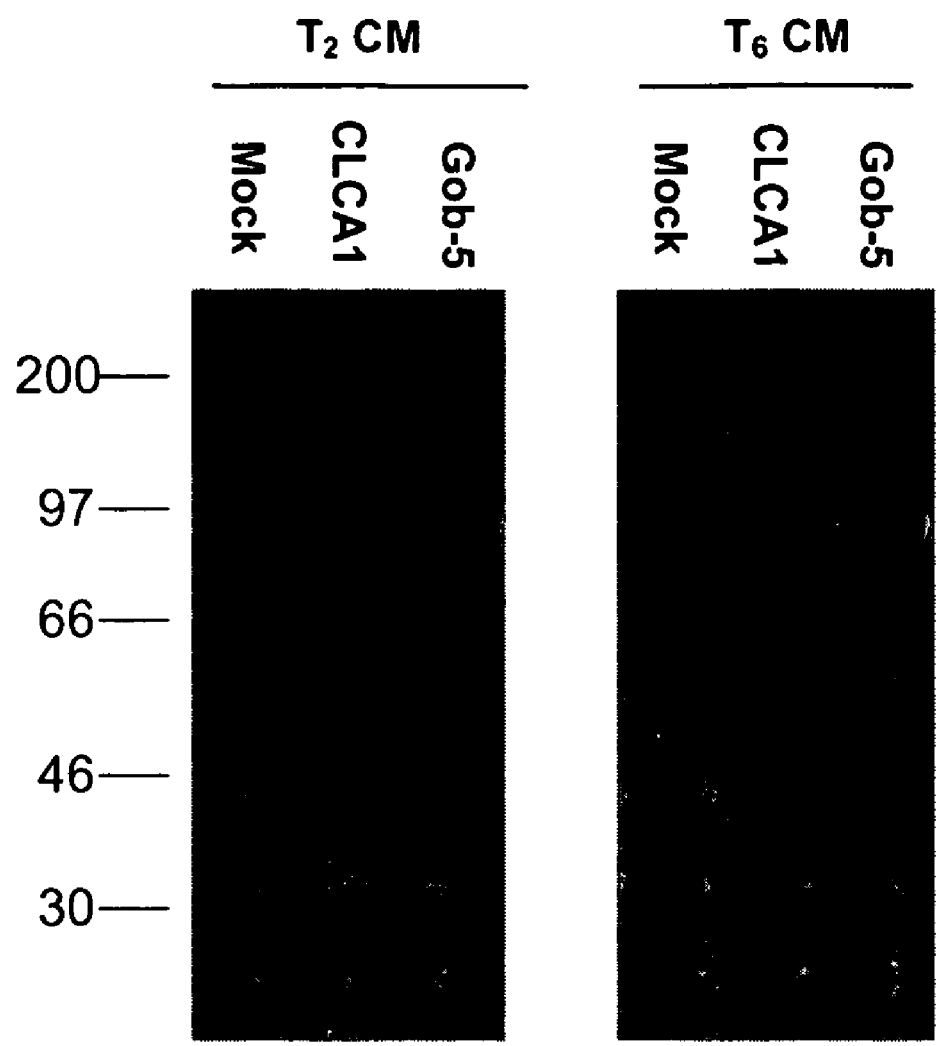
FIG. 2 demonstrates that both CLCA1 and gob-5 proteins are secreted from COS cells transfected to express the proteins.

Antibody, as used herein, means an immunoglobulin or a part thereof, and encompasses any polypeptide comprising an antigen-binding site regardless of the source, method of production, or other characteristics. The term includes for example, polyclonal, monoclonal, monospecific, polyspecific, humanized, single-chain, chimeric, synthetic, recombinant, hybrid, mutated, and CDR-grafted antibodies. A part of an antibody can include any fragment which can bind antigen, for example, an Fab, F(ab')$_2$, Fv, scFv.

The term "CLCA1," as used herein, refers to a protein that is not a membrane spanning protein. It can be covalently or non-covalently associated with a membrane or membrane associated molecule or a secreted molecule.

CLCA1 activity, as used herein, refers to modulation of an ion channel, e.g., a chloride channel.

The term "mucin", as used herein, refers to a fluid, e.g., secretion containing carbohydrate rich glycoproteins. Mucin can be secreted from the goblet cells of the intestines, the submaxillary glands or other glandular cells.

"Small molecule," as used herein, refers to any molecule having a molecular weight of less than 25 kD.

"Specific binding partner," as used herein, means a first molecule that specifically interacts with a second molecule. The interaction can be the result of a covalent bond, or a non-covalent bond, e.g., an ionic bond, a charge-charge interaction, a hydrophobic interaction, a hydrogen bond, or van der Waal's forces.

The term "subject," as used herein, means a human or a non-human mammal, e.g., a dog, a cat, a mouse, a rat, a cow, a sheep, a pig, a goat, a non-human primate.

The terms "treat," "treatment," and "treating," as used herein refers to any of the following: the reduction in severity of a disease or condition; the reduction in the duration of a disease course; the amelioration of one or more symptoms associated with a disease or condition; the provision of beneficial effects to a subject with a disease or condition, without necessarily curing the disease or condition; the prophylaxis of one or more symptoms associated with a disease or condition.

"Up-regulated," as used herein, refers to a protein expressed at levels in a subject having a disease or condition that are greater than the levels of the same protein in an individual who does not have the disease or condition.

Methods of Treatment

The invention relates to a method of treating a disease or condition where expression or activity of CLCA1 is up-regulated, comprising administration of at least one agent which inhibits or prevents CLCA1 association with a cell membrane molecule.

CLCA1 is a cellular protein implicated in diseases and conditions involving the up-regulation of mucin, e.g., atopic conditions such as asthma (FIG. 1; WO 99/44620). The present invention is based at least in part on the discovery that CLCA1 is a secreted protein that can interact, e.g., associate with an extra-cellular molecule, e.g., a cell membrane or a cell membrane associated molecule. By providing agents which inhibit or prevent CLCA1 from associating with membrane molecules and thus potentially increasing mucin production, the invention provides for a method of treating a disease or condition characterized by the up-regulation of mucin.

Thus, the invention relates to a method of treating a disease or condition wherein CLCA1 expression or activity is enhanced, e.g., up-regulated. The disease or condition can be an atopic or allergic disorder, e.g., asthma. The disease or condition can be any disease or condition wherein mucin levels are enhanced, e.g., mucin production and/or secretion is up-regulated. The disease or condition can be cystic fibrosis or COPD, i.e., emphysema, chronic bronchitis. The disease or condition can be one effecting any mucosal surface, e.g., a pulmonary surface or a gastro-intestinal surface. The disease or condition can be an infectious disease, e.g., a viral infection or a bacterial infection. The disease or condition can be either chronic or acute.

The methods of the invention employ an agent that specifically inhibits the activity of CLCA1, e.g., soluble CLCA1. In one embodiment, the agent binds directly to CLCA1, e.g. soluble CLCA1. In another embodiment, the agent inhibits, reduces or prevents CLCA1, e.g., soluble CLCA1 binding to an extra-cellular molecule, e.g., a membrane associated protein or lipid.

An agent which inhibits CLCA1 activity can include, but is not limited to, a protein or a protein fragment, e.g., a peptide. The protein or protein fragment can be recombinantly produced using known techniques, see, e.g., Sambrook et al. 1989, *Molecular Cloning: A Laboratory Manual*, 2d ed., Cold Spring Harbor Laboratory Press. Alternatively, the protein or protein fragment can be made by chemical synthesis using known techniques, see, e.g., Merrifield 1973, *Chemical Polypeptides*, (Katsoyannis and Panayotis eds.) pp. 335-61; Merrifield 1963, *J. Am. Chem. Soc.* 85:2149; Davis et al. 1985, *Biochem. Intl.* 10:394; Finn et al. 1976, *The Proteins*

($3^{rd}$ ed.) 2:105; Erikson et al. 1976, *The Proteins* (2nd ed.) 2:257; U.S. Pat. No. 3,941,763. The protein or protein fragment can be derivatized, e.g. pegylated. The protein or protein fragment can be fused to another protein to make a fusion protein, e.g., a GST fusion protein, an Fc fusion protein. The protein or protein fragment can be a glycoprotein or a lipoprotein. In one embodiment, the agent which inhibits CLCA1 activity is a CLCA1 specific binding partner.

The agent which inhibits CLCA1 activity can be a small molecule. The small molecule can be an organic molecule or an inorganic molecule. The small molecule can be synthesized using known techniques see, e.g., Morrison and Boyd, 1987, *Organic Chemistry* Fifth Edition, Allyn and Bacon, Newton, Mass.

In one specific embodiment the agent is an antibody or a fragment of an antibody. A fragment of an antibody can include, but is not limited to Fab, F(ab')$_2$, or a single chain Fv. The antibody can be a monoclonal antibody or a polyclonal antibody. In general, antibodies can be made, for example using traditional hybridoma techniques (Kohler and Milstein 1975, *Nature* 256:495), recombinant DNA methods (U.S. Pat. No. 4,816,567), or phage display performed on antibody libraries (Clackson et al. 1991, *Nature* 352:624; Marks et al. 1991 *J Mol Biol*, 222:581). For other antibody production techniques, see, *Antibodies: A Laboratory Manual*, eds. Harlow et al., 1988, Cold Spring Harbor Laboratory.

In vitro systems may be designed to identify compounds capable of inhibiting CLCA1 activity, e.g., by binding to CLCA1. The assay can involve preparing a reaction mixture of CLCA1 and a test compound under conditions, and for a time, sufficient to allow a complex to form. The complex can be a transient complex and the complex can be removed or detected in the reaction mixture. CLCA1 can be anchored to a solid phase, e.g., a bead, a microtiter plate, and then reacted with the test agent and the complex detected. Alternatively, the test agent can be anchored to a solid phase, and reacted with CLCA1 and the complex detected. Unreacted reagents can be washed away. The non-anchored species can be labeled directly or indirectly. Labels can include, for example, but not as a limitation, dyes, chromophores or radioactivity. The label can be conjugated to an antibody specific to the test agent or CLCA1.

In one embodiment, mucin production can be used to measure CLCA1 activity in the presence or absence of a test CLCA1 inhibitory agent. Mucin production can be measured in vitro using a muco-epidermal cell line, e.g., NCl—H292 transfected with the human CLCA1 gene (see Nakanishi et al. 2001, *Proc Natl Acad Sci USA* 98(9):5175). A test agent inhibitor can be added to the media and mucin production monitored. Mucin production can be monitored using techniques well known in the art, e.g., ELISA, SDS-PAGE, or Western blot.

The CLCA1 inhibitor can be administered intravenously, subcutaneously, sublingually, intramuscularly, orally, buccally, nasally, rectally, or via pulmonary route. The CLCA1 inhibitor can be implanted within or linked to a biopolymer solid support that allows for the slow release of the chimeric protein.

The CLCA1 inhibitor can be administered in combination with a therapeutically effective amount of a second agent known in the art for the treatment of a condition or disease. As an example, but not as a limitation, asthma can be treated with a CLCA1 inhibitor and a beta-receptor agonist or a corticosteroid.

The dose of the CLCA1 inhibitor will vary depending on the subject and upon the particular route of administration used. Dosages can range from 0.1 to 100,000 µg/kg body weight. In one embodiment, the dosing range is 1-10 mg/kg. The CLCA1 inhibitor can be administered continuously or at specific timed intervals. In vitro assays may be employed to determine optimal dose ranges and/or schedules for administration. Additionally, effective doses may be extrapolated from dose-response curves obtained from animal models, e.g., murine asthma (see Nakanishi et al. 2001, *Proc Natl Acad Sci USA* 98(9):5175).

The invention also relates to a pharmaceutical composition comprising CLCA1 inhibitors and a pharmaceutically acceptable carrier or excipient. Examples of suitable pharmaceutical carriers are described in *Remington's Pharmaceutical Sciences* by E. W. Martin. Examples of excipients can include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol, and the like. The composition can also contain pH buffering reagents, and wetting or emulsifying agents.

For oral administration, the pharmaceutical composition can take the form of tablets or capsules prepared by conventional means. The composition can also be prepared as a liquid for example a syrup or a suspension. The liquid can include suspending agents (e.g., sorbitol syrup, cellulose derivatives or hydrogenated edible fats), emulsifying agents (lecithin or acacia), non-aqueous vehicles (e.g., almond oil, oily esters, ethyl alcohol, or fractionated vegetable oils), and preservatives (e.g., methyl or propyl-p-hydroxybenzoates or sorbic acid). The preparations can also include flavoring, coloring and sweetening agents. Alternatively, the composition can be presented as a dry product for constitution with water or another suitable vehicle.

For buccal and sublingual administration the composition may take the form of tablets or lozenges according to conventional protocols.

For administration by inhalation, the compounds for use according to the present invention are conveniently delivered in aerosol form, e.g., an aerosol spray from a pressurized pack or nebulizer, with a suitable propellant, e.g., dichlorodifluoromethane, trichlorofluoromethane, dichlorotetrafluoromethane, carbon dioxide or other suitable gas. In the case of a pressurized aerosol the dosage unit can be determined by providing a valve to deliver a metered amount. Capsules and cartridges of, e.g., gelatin for use in an inhaler or insufflator can be formulated containing a powder mix of the compound and a suitable powder base such as lactose or starch.

The pharmaceutical composition can be formulated for parenteral administration (i.e., intravenous or intramuscular) by bolus injection. Formulations for injection can be presented in unit dosage form, e.g., in ampoules or in multidose containers with an added preservative. The compositions can take such forms as suspensions, solutions, or emulsions in oily or aqueous vehicles, and contain formulatory agents such as suspending, stabilizing and/or dispersing agents. Alternatively, the active ingredient can be in powder form for constitution with a suitable vehicle, e.g., pyrogen free water.

The pharmaceutical composition can also be formulated for rectal administration as a suppository or retention enema, e.g., containing conventional suppository bases such as cocoa butter or other glycerides.

Methods of Isolating CLCA1

CLCA1 is a secreted soluble protein. Accordingly, it is readily isolated from any fluid containing it by contacting the fluid with a specific binding partner of CLCA1.

CLCA1 can be isolated from any biological fluid. A biological fluid can include any body fluid or secretion. In one embodiment, CLCA1 is isolated from sputum. In another embodiment, CLCA1 is isolated from bronchial alveolar lavage. The bodily fluid can be obtained from any mucosal surface. In one embodiment, the mucosal surface is a pulmonary surface or a rectal surface.

A specific binding partner can include, but is not limited to, a protein or a protein fragment, e.g., a peptide. The protein or protein fragment can be derivatized, e.g., pegylated. The protein or protein fragment can be part of a fusion protein, e.g., a GST fusion protein, an Fc fusion protein. The protein or protein fragment can be a glycoprotein or a lipoprotein. The specific binding partner can be a small molecule. The small molecule can be an organic molecule or an inorganic molecule. In one specific embodiment the agent is an antibody or a fragment of an antibody. A fragment of an antibody can include, but is not limited to Fab, $F(ab')_2$, or a single chain Fv. The antibody can be a monoclonal antibody or a polyclonal antibody.

Soluble CLCA1 can be isolated by reacting it with a specific binding partner under a first set of conditions such that a complex forms between CLCA1 and the specific binding partner. The reaction can occur in a liquid phase and the complex isolated by contacting it with an antibody which recognizes the specific binding partner. Alternatively, the specific binding partner can be linked to a solid support, either directly or indirectly, e.g., by an antibody which recognizes the specific binding partner. The solid support can be, for example, but is not limited to, a bead, a microtiter plate, a matrix of a column, a membrane, or a monolith. Once the complex has formed, the reaction conditions can be changed, e.g., by changing the pH, or by changing the salt concentration of the solution containing the complex, to a second set of conditions such that the complex is disrupted. The specific binding partner remains bound to the solid support, thus providing a solution containing isolated CLCA1.

EXAMPLES

Example 1

Transient Expression of CLCA1 and Gob-5 in COS-7 and HEK293 Cells

COS and HEK293 cells were maintained in Dulbecco's modified Eagle's (DME) medium supplemented with 10% (v/v) fetal calf serum (FCS), 50 units/ml penicillin, 50 µg/ml streptomycin and 2 mM glutamine and grown in a humidified atmosphere at 37° C. At 16 hours prior to transfection, COS cells were seeded in a 100 mm tissue culture treated dish at $4 \times 10^6$ cells per dish. After cells had reached approximately 70% confluence, 10 µg of DNA was mixed with Lipofectamine 2000 reagent (Invitrogen, Carlsbad, Calif.) in Opti-MEM serum free medium (Life Technologies, Carlsbad, Calif.) as described in the manufacturer's instructions. Lipofectamine 2000/DNA mixture was added to the culture medium of the COS cells for 6 hours at 37° C. After the incubation period, the medium in the plate was replaced with complete medium (DME 10% FCS). Cells were allowed to incubate at 37° C. for 24-48 hours after which the conditioned media and cell lysates were harvested for biochemical analysis.

Example 2

Radioactive Incorporation into Heterologously Expressed Protein

COS cell monolayers transfected with CLCA1, gob-5, or pcDNA3.1 vector control were incubated for 20 minutes in serum free DME without cysteine or methionine. The cells were then labeled with 300 µCi of Promix (Amersham, Piscataway, N.J.), a mixture of $^{35}S$ labeled cysteine and methionine, per 100 mm dish for 30 minutes. The radioactive amino acid containing medium was removed and the cells were washed 3 times with PBS. Radioactive waste was disposed of in accordance Nuclear Regulatory Commission guidelines. DME with 10% v/v fetal calf serum was added and cells were incubated for 2 to 6 hours at 37° C. At these time points, conditioned media and cell lysates were harvested. Incorporated radioactivity was determined by TCA precipitation as follows. For each sample, 1 µl was blotted onto a small piece of Whatman 3MM paper. Sample paper was immersed in ice-cold 10% w/v trichloracetic acid (TCA) for 10 minutes. The samples were washed 3 successive times for 5 minutes each with ice-cold ethanol and then allowed to air dry. Once dry, paper samples were added to 10 ml of Scinti-Safe (Fisher Scientific, Hanover Park, Ill.) scintillation fluid in scintillation vials. Levels of radioactivity were measured in a Beckman Scintillation Counter.

Example 3

Harvesting of Cell Lysates

Cell monolayers were washed twice with ice-cold, calcium and magnesium free, phosphate buffered saline (PBS). Cells were removed from the dish using 0.25% (v/v) Trypsin-EDTA (Gibco, Carlsbad, Calif.) and counted using a hemacytometer. The cells were washed twice with ice cold PBS and lysed in NP-40 lysis buffer (1% NP-40, 50 mM HEPES, 150 mM NaCl, 1 mM EDTA, 10% glycerol) for 15 minutes on ice at a concentration of $0.5 \times 10^6$ cells/10 µl of lysis buffer. The resulting lysate was cleared by microcentrifugation at 15000 RPM for 15 minutes and then stored at −80° C. until used in Western blots.

Example 4

Membrane Preparations

COS cells grown in 100 mm tissue culture treated dishes were transfected as described in Example 1. 48 hours after transfection, cells were removed from the plate with trypsin and washed twice with cold PBS in a 50 ml tube. The cells were resuspended in 4 ml of 1 mM Tris pH 7.4 and left on ice for 20 minutes. The cell suspension was homogenized with 10 strokes of a clean dounce homogenizer. The samples were then spun at 2000 g in a Sorvall Legend RT table top centrifuge for 10 minutes. The supernatant was transferred to an ultracentrifuge tube and spun by ultracentrifugation at 100,000 g for 1 hour. The resultant pellet was suspended in 100 µl of NP40 lysis buffer.

Example 5

Western Blotting

Samples were combined with 2×SDS sample buffer with β-mercapatoethanol and boiled for 2 minutes. After boiling, the samples were loaded onto either a 4-20% gradient gel or 6% SDS gel. Gels were then transferred to nitrocellulose using an Invitrogen blotting apparatus (Invitrogen, Carlsbad, Calif.) and transfer buffer as provided by Invitrogen (Invitrogen, Carlsbad, Calif.). Gels were transferred for 2 hours at 30V under constant current. Nitrocellulose blots were blocked in 5% non-fat dry milk for 1 hour at room temperature. The blots were incubated with 0.5 µg/mL peptide polyclonal antibody overnight at 4° C. After incubation with the primary antibody, the blots were washed 3 times for 10 minutes each in washing buffer (1% Triton×100 (v/v), 0.1% SDS (w/v) in PBS, calcium and magnesium free) and then incubated for 30 minutes with mouse anti rabbit IgG conjugated to horseradish peroxidase (Santa Cruz Biotech, Santa Cruz, Calif.). The blots were washed 3 times for 10 minutes each in wash buffer and developed with the chemiluminescence reagent, ECL. (Amersham, Piscataway, N.J.). The blots were exposed to Kodak film and developed using a film developer.

Example 6

Generation of Constructs

CLCA1 was isolated from human colon cDNA using polymerase chain reaction (PCR). The 5' anchoring primer used in the reaction was as follows: 5'-CGCAAGCTTG GGATGGGGCC ATTMGAGT TCTGTGTTC-3' (SEQ ID NO:1). The underlined sequence represents a HindIII restriction endonuclease site. All constructs used this 5' primer. The 3' primer used in deletion constructs were as follows: (1-708) 5'-CCCMGCTTT CACTACTTAT TMTTTCAGG TCTTG-GTGG-3' (SEQ ID NO: 2), (1-660) 5'-CCCAAOCTTT CAC-TACCTTG AGTAGACACC GTCATCCTTA G-3' (SEQ ID NO: 3) and (1-462) 5'-CCCMGCTTT CACTATTGAT CTG-MGCATA TGTCTGTAAA CCTCCCTG-3' (SEQ ID NO: 4). PCR products were amplified with high fidelity Taq DNA polymerase (Invitrogen, Carlsbad, Calif.). Deletion constructs used wild-type CLCA1 as a template. The template was denatured for 2 minutes at 96° C. and then the reaction proceeded as follows: the DNA was denatured at 94° C. for 30 seconds, annealed at 65° C. for 1 minute, and extended at 72° C. for 1 minute. This cycle was repeated for 20 cycles. The resulting product was digested with HindIII. pcDNA3.1 was digested with HindIII and dephosporylated with calf intestinal alkaline phosphatase (New England Biolabs, Beverly, Mass.). Fragments were ligated using Rapid DNA ligation kit (Roche, Basel, Switzerland) and then transformed with One Shot chemically competent *E. coli* (Invitrogen, Carlsbad, Calif.).

Example 7

Generation of Polyclonal Antibodies

Peptide polyclonal antibody generation was performed at Invitrogen (Carlsbad, Calif.) according to the protocol described herein. New Zealand white rabbits (age 3-9 months) were immunized with KLH-peptide (see below) emulsified in Freund's Adjuvant by subcutaneous injections at three dorsal sites (0.1 mg peptide per immunization). Animals were bled by articular artery. Serum was collected and titer was determined via free peptide ELISA. Five hydrophilic peptides were selected based on extracellular domains as previously described (Nakanishi et al. 2001, *Proc Natl Acad Sci USA* 98:5175). The hyrdophillic peptides included 1CLC, corresponding to amino acids 124-140, Gly Glu Lys Gly Glu Arg Ile His Leu Thr Pro Asp Phe Ile Ala (SEQ ID NO: 5); 2CLC, corresponding to amino acids 202-217, Glu Gin Asn His Asn Lys Glu Ala Pro Gin Lys Gln Asn Gln Lys; 3CLC (SEQ ID NO: 6), corresponding to amino acids 478-495, Gly Gln Gly Val Ser Gln Arg Ser Ile Gln Leu Glu Ser Lys Gly Leu Thr (SEQ ID NO: 7); 4CLC, corresponding to amino acids 702-719, lie Glu Asn Asp Glu lie Gln Trp Asn Pro Pro Arg Pro Glu Ile (SEQ ID NO: 8); and 5CLC, corresponding to amino acids 819-833, Lys Glu Ala Asn Ser Glu Glu Val Phe Leu Phe Lys Pro Glu Asn (SEQ ID NO: 9).

Example 8

PNGase F Treatment

PNGase F was obtained from New England Biolabs (Beverly, Mass.) and was used according to the manufacturer's instructions. Samples were boiled in reducing buffer for 5 minutes. Ethylphenyl-polyethylene glycol (NP-40) was added to a final concentration of 1% (v/v) along with 1×G7 reaction buffer (New England Biolabs, Beverly, Mass.)). 1 µl of PNGase F was added and incubated for 1 hour at 37° C. 2× sample buffer (Invitrogen, Carlsbad, Calif.) was then added and samples were resolved on Tris-glycine gels as described in Example 5.

Example 9

MUC5AC Reporter Assay

A 1.6 kilobase fragment of the MUC5AC promoter was fused to the firefly luciferase gene used as a reporter (MUC5AC-luc). A549 cells were transfected in 6-well tissue culture treated plates with Fugene transfection reagent (Roche, Basel, Switzerland) using a total of 2 µg per well. 0.5 µg of MUC5AC-luc construct was used per well. Varying concentrations of CLCA1 or deletion constructs were used to establish a dose response. Vector DNA (pcDNA3.1) was used to complete DNA total to 2 µg. The cells were washed twice and transfected for 6 hours in serum free Hams/F12 media (Life Technologies, Carlsbad, Calif.). After 6 hours, the media was changed to serum containing, i.e., 10% serum Hams/F12. The cells were lysed in cell lysis solution provided with the luciferase assay reagents (Promega, Madison, Wis.) and the manufacturer's instructions were followed. The samples were transferred in triplicate to a 96-well plate and were read on a 96-well luminometer (Turner Biosystems, Sunnyvale, Calif.).

Example 10

Computational Analysis of CLCA1

CLCA1 is a 914 amino acid polypeptide that contains nine putative N-linked glycosylation sites (FIG. 1). A hydrophobic stretch of 21 residues is predicted to be a secretory signal sequence according to the algorithm SigCleave. The CLCA1 polypeptide sequence was also used to query the NCBI Conserved Domain Database (http://www.ncbi.gov) and discovered to contain a central von Willebrand factor A-domain (VWA) that spans 270 amino acids. The VWA domain of CLCA1 contains an intact MIDAS motif, a defined set of amino acids responsible for binding of divalent metal cations.

CLCA1 was evaluated using the transmembrane hidden Markov model (TMHMM) (Sonnhamer et al. 1998, Proc Sixth Int Conf on Intelligent Systems for Molecular Biology, AAAI Press). The model was developed as a tool to analyze membrane spanning alpha helices and to predict not only membrane spanning segments but also membrane topology as well. The TMHMM suggests that CLCA1 will have no transmembrane segments just like the secreted protein, serum albumin (FIG. 4). To ensure that the models are predictive, other proteins with well understood transmembrane topology or solved crystal structure were analyzed. The model consistently predicted the 12 hydrophobic segments of CFTR and the defined hydrophobic stretches of CLC from *E. coli* (Riordan et al. 1989, *Science* 254:1606; Dutzler et al. 2002, *Nature*

415:287). Based on another hydrophobicity model, Split 4.0 (http://pref.effos.hr/split-4.0/), CLCA1 is also predicted to be a soluble protein (FIG. 5).

Example 11

Heterologous Expression of CLCA1

Figure 3:
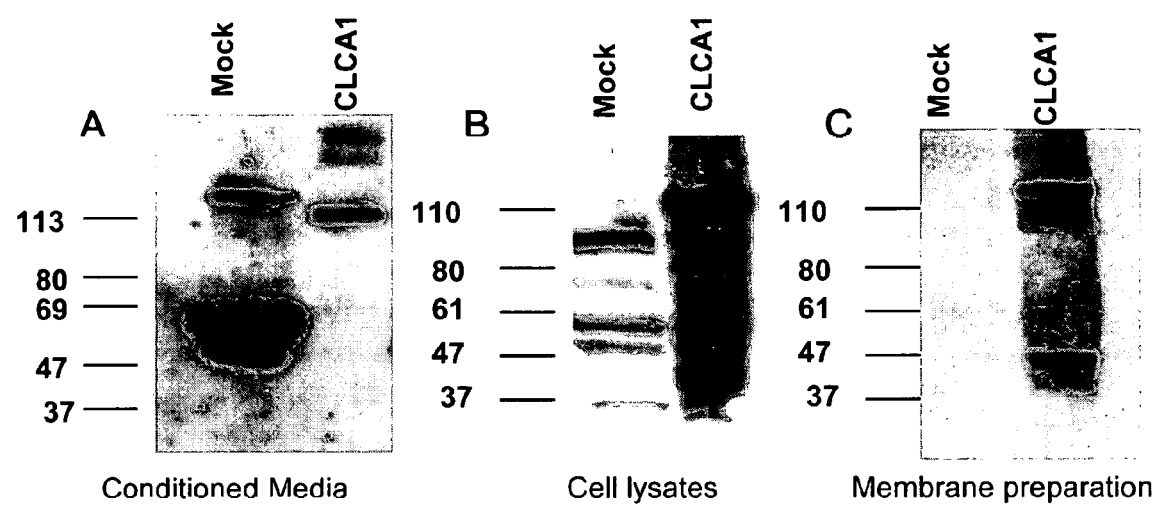
FIG. 3 is a Western blot demonstrating the presence of CLCA1 in conditioned media, cell lysate and membrane preparation of cells transfected to express CLCA1.

To examine its cellular localization, CLCA1 was heterologously expressed in COS-7 cells and HEK293 cells using the mammalian expression vectors pcDNA3.1 and pDEST 12.2. Overexpression of CLCA1 yielded a surprising 120 kD species in the culture medium as measured by $^{35}$S cys-met radioactive incorporation (FIG. 2). The presence of these bands in the culture media suggests CLCA1 is secreted. To confirm the identity of CLCA1, peptide polyclonal antibodies were generated against peptides that corresponded to extracellular domains as suggested by Gruber (Gruber et al. 1999, Genomics 54:200) for use in western blot analysis. The secreted phenotype was indeed confirmed by Western blotting, which revealed a CLCA1 immunoreactive band of 120 kD in conditioned media of both COS-7 transfected cells and HEK293 transfected cells (FIG. 3A). The presence of full length CLCA1 was confirmed in the conditioned media. A 120 kD band and a 37 kD band were also seen in the cell lysate by Western blot (FIG. 3B). These bands were not present in vector control transfected cells.

Membrane preparations were analyzed to test whether the bands present in the cell lysates are from the secretory pathway or associated with the membrane. Both the 120 kD and the 37 kD bands are associated with the membrane (FIG. 3C). Conditioned media samples from vector and CLCA1 transfected HEK293 cells were analyzed by mass spectrometry to verify the specificity of the polyclonal antibodies. The CLCA1 immunoreactive bands in the Western blots were confirmed to be full length CLCA1.

Figure 6:
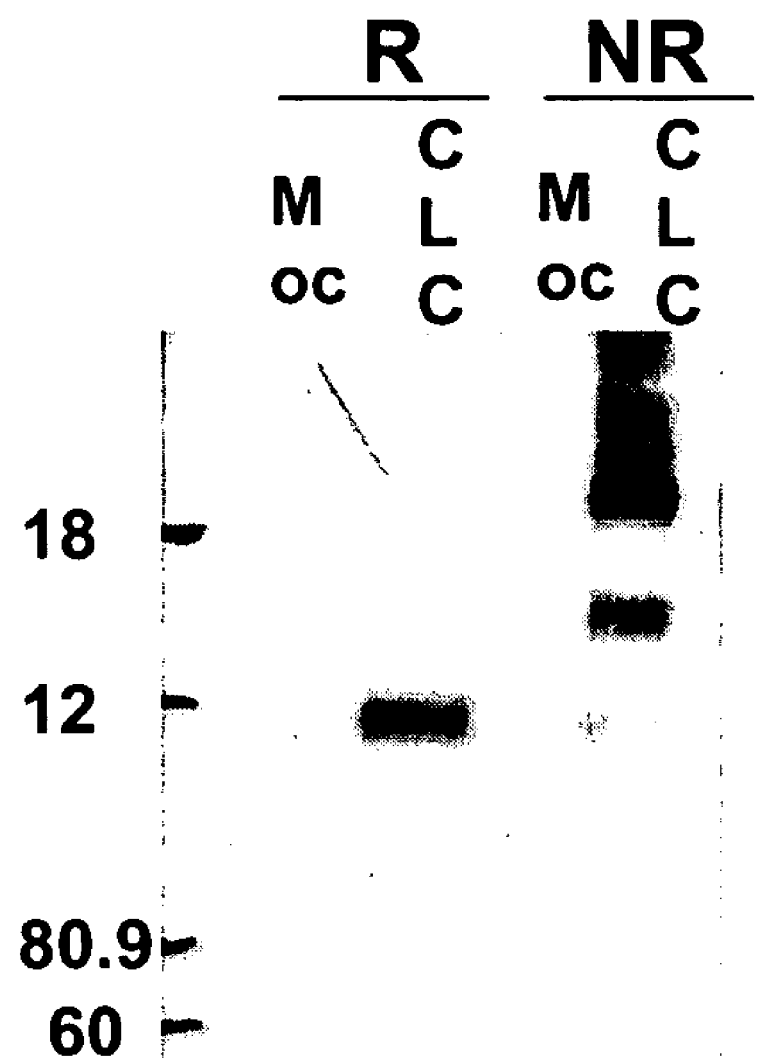
FIG. 6 is a Western blot demonstrating that CLCA1 is secreted as a multimer.

The conditioned media from both COS and HEK293 transfectants were analyzed by Western blot under reducing and non-reducing conditions to assess whether CLCA1 exists as a multimer in the secreted milieu. Under reducing conditions, CLCA1 migrates at a size of approximately 120 kD. Under non-reducing conditions, higher species consistent with dimer formation become apparent (FIG. 6). These observations were made using 4-20% gradient Tris-Glycine SDS gels. To increase resolution, 6% Tris-Glycine gels were used. CLCA1 migrates, under non-reducing conditions, at sizes consistent with dimer and multimer formation.

Figure 7:
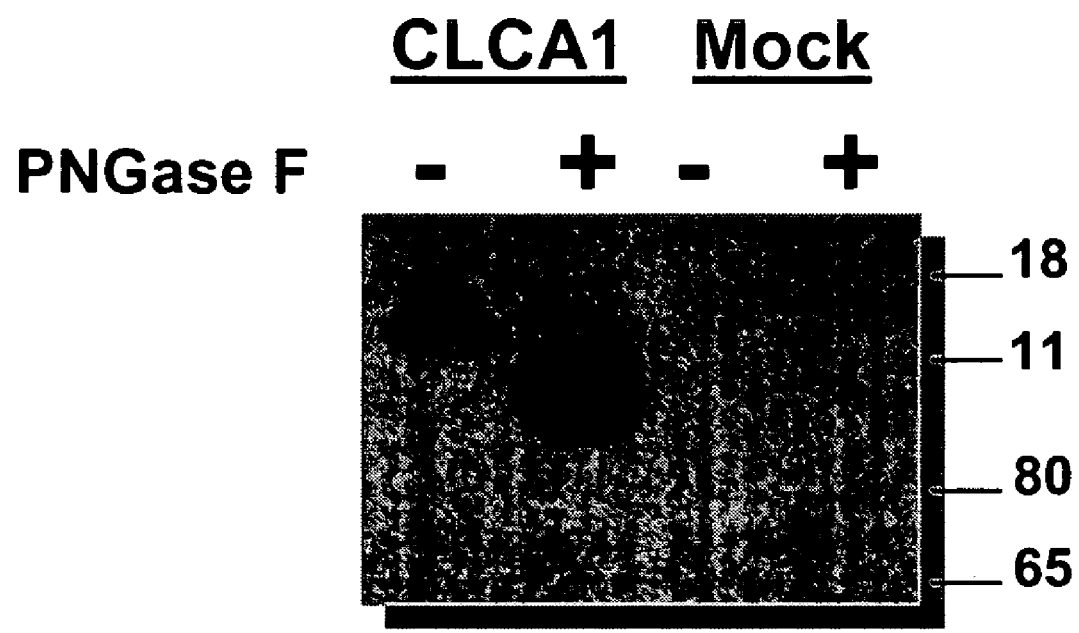
FIG. 7 demonstrates that CLCA1 is highly glycosylated. PNGase treatment reduces the size of the secreted protein.

Based on the primary protein sequence, CLCA1 is predicted to have a molecular weight of approximately 100 kD. Analysis by SDS-PAGE reveals a species in the conditioned media that migrates at 120 kD. CLCA1 has nine putative N-linked glycosylation sites (FIG. 1). Secreted samples were treated with the N-glycosidase PNGase F to determine the contribution of the N-linked sugars to the molecular weight discrepancy. Treatment with PNGase F reduced the size to the expected 100 kd (FIG. 7). This is consistent with the fact that CLCA1 has nine putative N-linked glycosylation sites (FIG. 1) and may be highly glycosylated.

Figure 8:
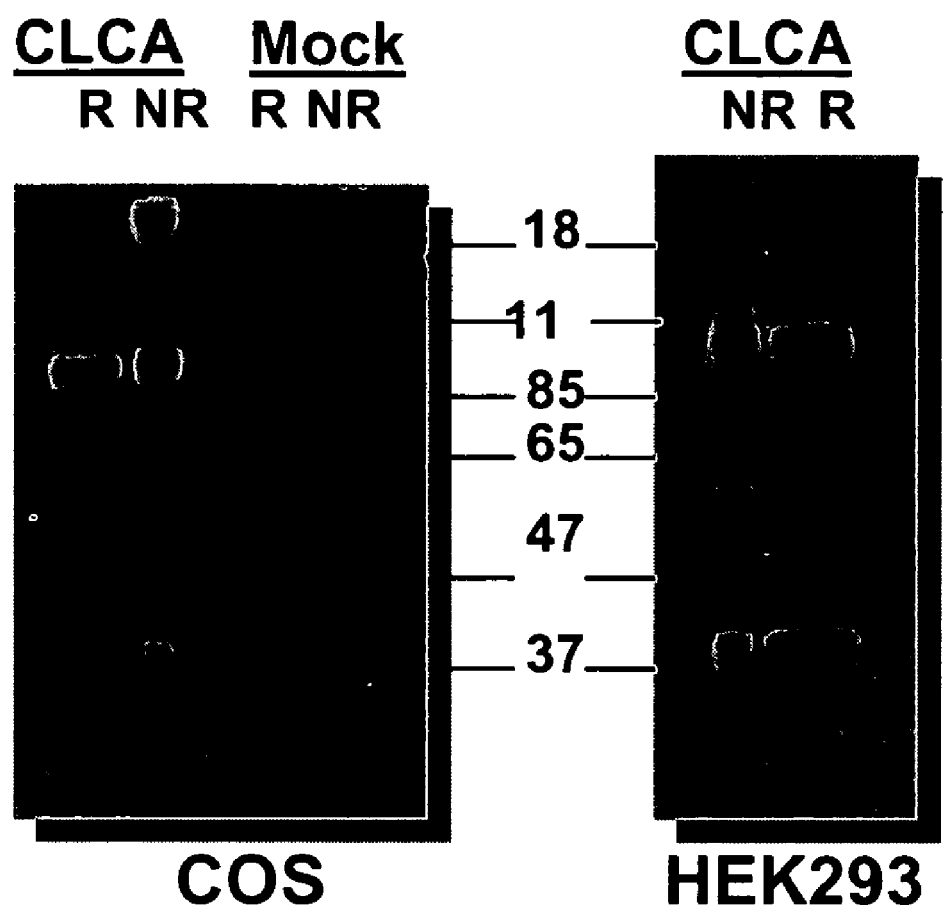
FIG. 8 is a Western blot demonstrating that the subunits of CLCA1 are not linked by a disulfide bond.

Gruber et al. suggest that CLCA1 is cleaved from its full length 120 kD product to yield a 90 kD and 37 kD product, which are associated via disulfide linkage (Gruber et al. 1999, Genomics 54:200). To test whether the two subunits are linked via disulfide linkage, lysates were run on Western blot under reducing and non-reducing conditions (FIG. 8). Under non-reducing conditions, the 37 kD species is still present. This observation would suggest that disulfide linkages do not associate with the lower subunit.

Example 12

Native Expression of Soluble CLCA1

Because the secreted phenotype of CLCA1 was seen primarily in overexpression systems, there was a concern that the phenomenon was an artifact of aberrant cellular processing. Gene expression studies have suggested that CLCA1 is expressed in the lungs after antigen challenge. As a result, bronchial alveolar lavage (BAL) fluid from cynomologous monkeys challenged with *Ascaris suum* was tested by Western blot for the presence of soluble CLCA1. Immunoreactive bands of 90 kD and 120 kD were detected in the BAL from both unchallenged and challenged states in the same animals.

Figure 9:
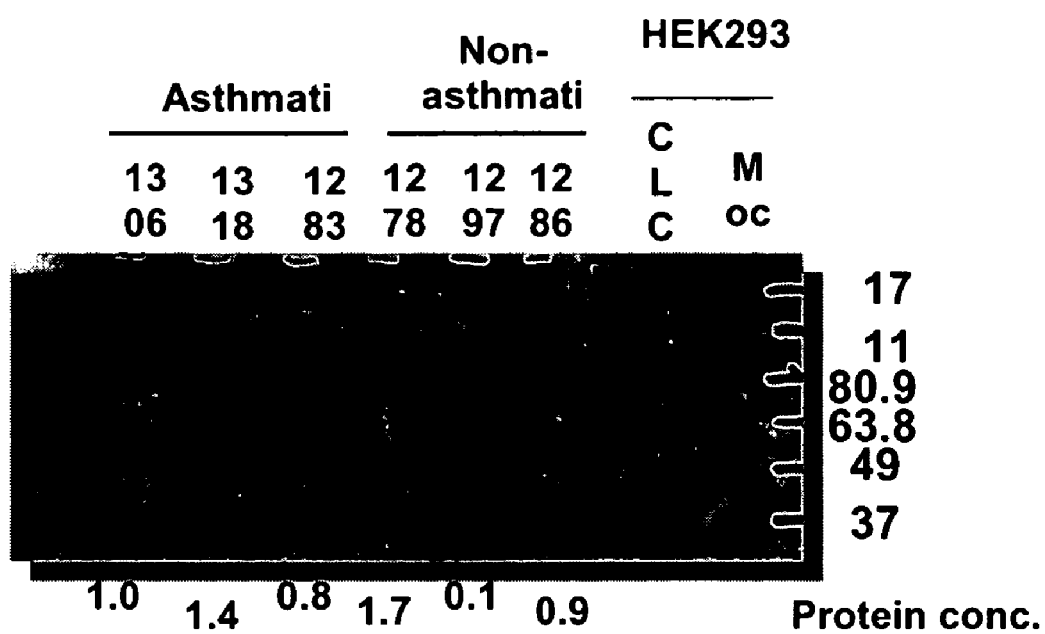
FIG. 9 demonstrates that CLCA1 is present in the BAL fluid of asthmatic and non-asthmatic patients.

Next, samples of human BAL were tested from both asthmatic and non-asthmatic patients. The results obtained from the human samples were similar to the results obtained from the monkey BAL samples. Consistently, there were two bands at 90 and 120 kD. There was variability from patient to patient but overall, there did not seem to be any difference in protein expression between asthmatic and non-asthmatic samples (FIG. 9).

Figure 10:
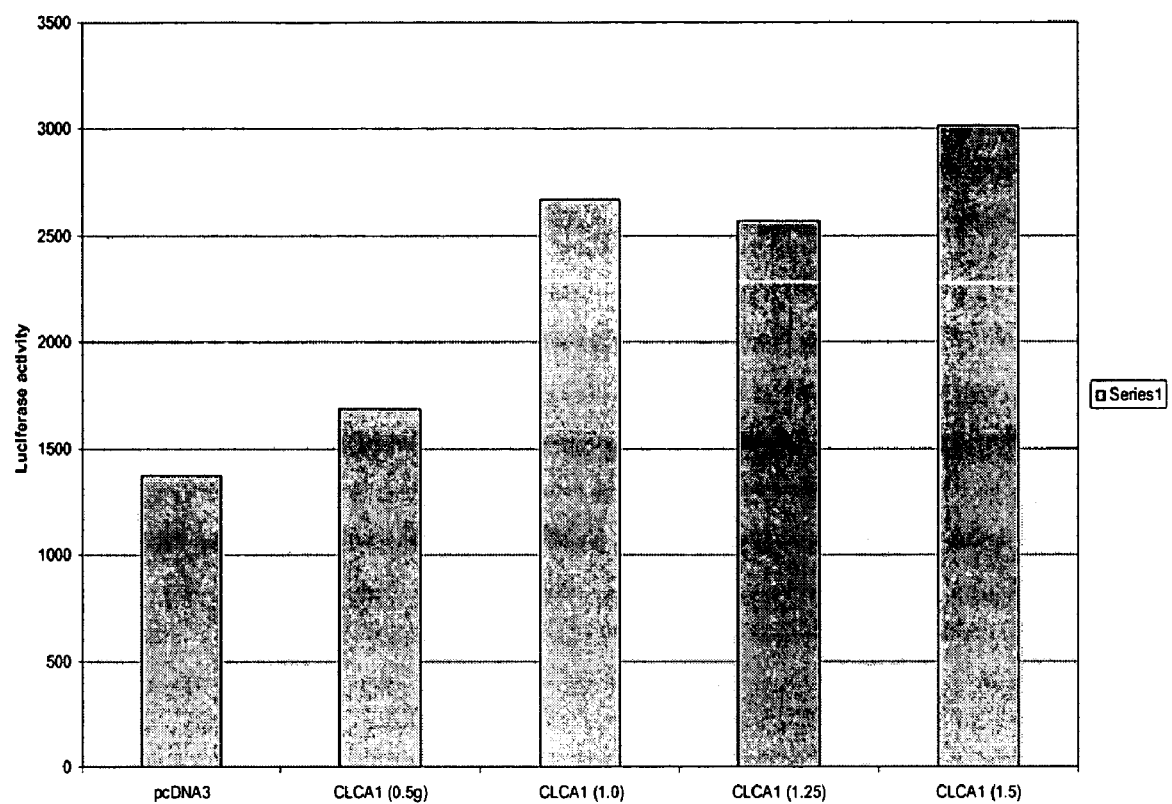
FIG. 10 demonstrates that CLCA1 activates the MUC5AC promoter in a dose dependent manner.

Based on expression studies and the physiologic observation that induction of CLCA1 resulted in mucus production (Hoshino et al. 2002, *Am J Respir Crit Care Med* 165:1132; Nakanishi et al. 2001, *Proc Natl Acad Sci USA* 98:5175), a reporter assay was developed that used the MUC5AC gene promoter fused to the firefly luciferase gene as an assay readout. A549 cells were used because of their mucoepidermal and respiratory tract origins. Overexpression of CLCA1 in A549 cells results in a dose dependent increase in MUC5AC gene transcription as measured by luciferase activity (FIG. 10).

Example 13

Generation of Constructs

Figure 11:
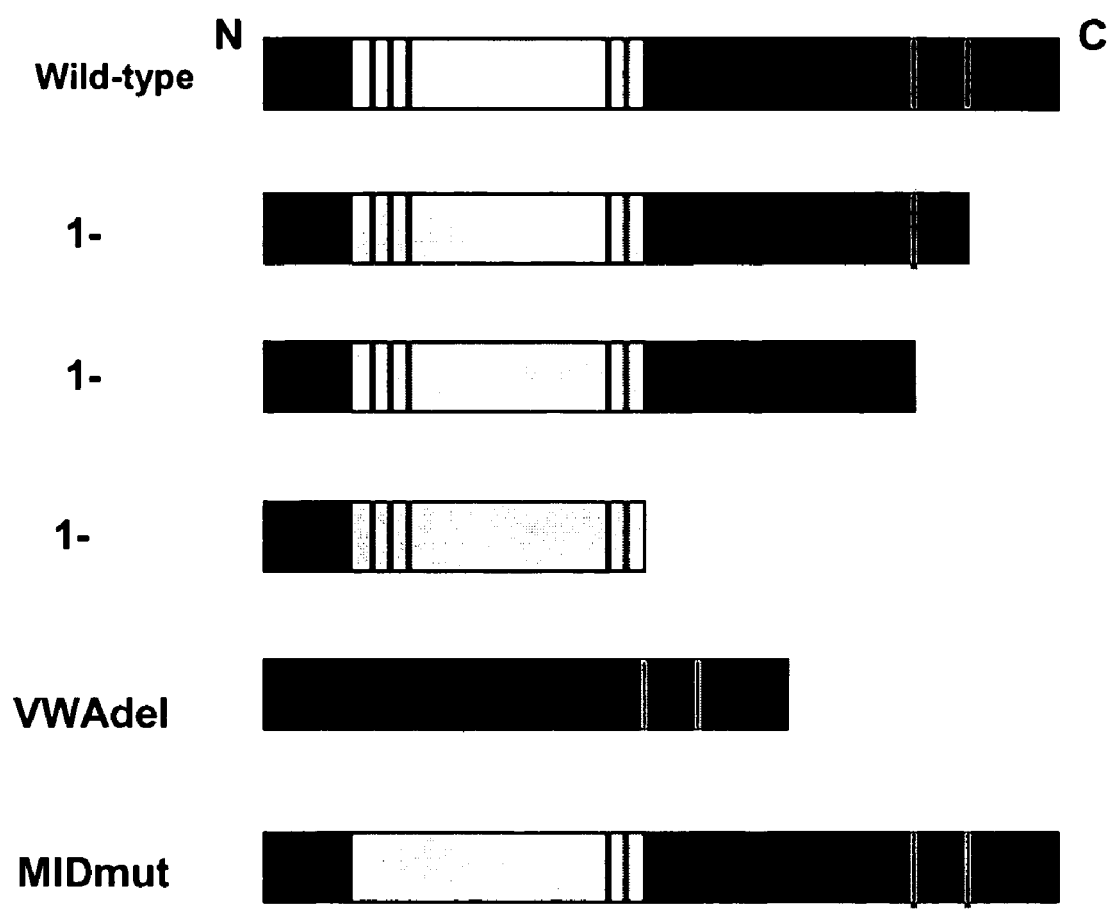
FIG. 11 depicts a schematic diagram of CLCA1 deletion mutants showing the location of VWA domain, MIDAS domain residues and proposed cleavage sites.

Deletion and mutation constructs will be made to identify the functional determinants of CLCA1 (FIG. 11). C-terminal deletion constructs will have deleted amino acids 709-914 and 661-914, which correspond to putative cleavage products as proposed by Gruber et al. (Gruber et al. 1999, *Genomics* 54:200). Construct 1-462 will be comprised of the N-terminus including the VWA domain. VWAdel will be comprised of the entire molecule with the VWA domain deleted. This will test the necessity of the VWA domain for the function of CLCA1. Additionally, the MIDAS motif of the VWA domain, which is necessary for divalent cation binding, will be mutated to eliminate that binding.

Example 14

Expression of CLCA1 and Gob-5 in HEK293 and A549 Cells

Figure 14:
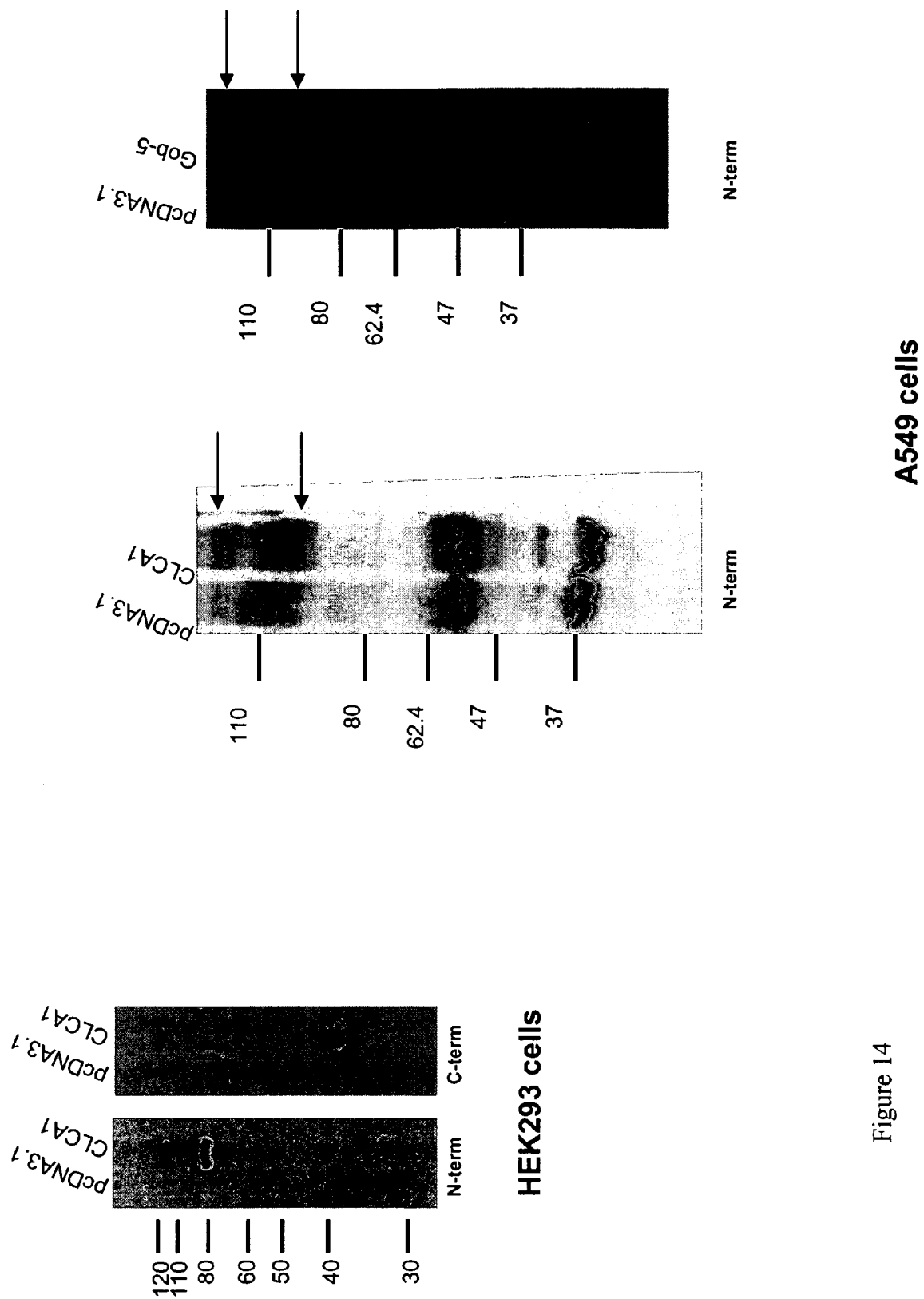
FIG. 14 is a western blot showing CLCA1 and gob-5 expression in HEK293 cells and in A549 cells.

The pneumocyte cell line A549 and the embryonic kidney cell line HEK293 were each transfected with a plasmid, pcDNA3, engineered to encode either CLCA1 or gob-5. Expression was confirmed by Western blot. Samples were combined with 2×SDS sample buffer with β-mercapatoethanol and boiled for 2 minutes. After boiling, the samples were loaded on either 4-20% gradient or 6% SDS gels. Gels were then transferred to nitrocellulose using an Invitrogen blotting apparatus and transfer buffer (Invitrogen, Carlsbad, Calif.). Gels were transferred for 2 hours at 30V under constant current. Nitrocellulose blots were blocked in 5% (w/v) nonfat dry milk for 1 hour at room temperature. Blots were incubated overnight at 4° C. with peptide polyclonal antibody which recognized either the N or C terminus of CCLA1 or gob-5. After incubation with the primary antibody, blots were washed 3 times for 10 minutes each in washing buffer (1% (v/v) Triton X 100, 0.1% (w/v) SDS in PBS-calcium and magnesium free) and then incubated for 30 minutes with mouse anti-rabbit IgG conjugated to horseradish peroxidase. Blots were washed 3 times for 10 minutes each in wash buffer and developed with a chemiluminescence reagent (ECL reagent)(Amersham, Uppsala, Sweden). Blots were exposed to Kodak film and developed using a film developer. The results showed that both CLCA1 and gob-5 were expressed (FIG. 14).

Example 15

CLCA1 and Gob-5 Induce MUC5AC Gene Transcription

A construct (MUC5AC-luc) comprising a 1.6 kb fragment of the MUC5AC promoter fused upstream of the reporting gene, luciferase, was used to determine if the overexpressed CLCA1 or gob-5 could induce gene expression under the control of a mucin promoter.

A549 or HEK293 cells were transfected in 6-well tissue culture treated plates with TransIT transfection reagent (Mirus Corp., Madison, Wis.) using a total of 4 mg per well. MUC5AC-luciferase construct (0.2 mg/well) was transfected into HEK293 cells. 1 mg of MUC5AC-luciferase construct was used per well for A549 cells. Twenty-four hours after transfection, the cells were lysed in cell lysis solution provided with luciferase assay reagents (Promega, Madison, Wis.) and the manufacturer's instructions were followed. Samples were transferred in triplicate to a 96-well plate and were read on a 96-well luminometer (Turner Biosystems, Sunnyvale, Calif.). Luciferase data presented was normalized for β-galactosidase expression (HEK293 cells) or per mg total protein (A549 cells).

Figure 12A:
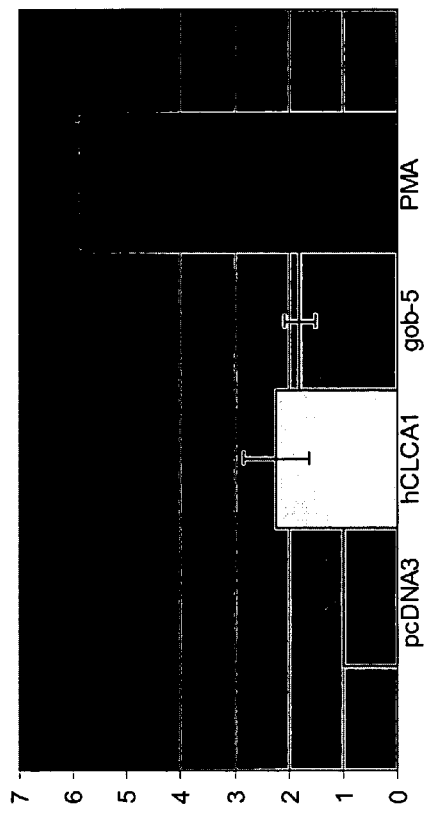
FIG. 12a shows MUC5AC-luciferase reporter induction by over-expression of CLCA1 or gob-5 in A549 cells. CLCA and gob-5 show a 2 fold induction of MUC5AC-luciferase reporter activity as compared to vector transfected controls.
Figure 12:
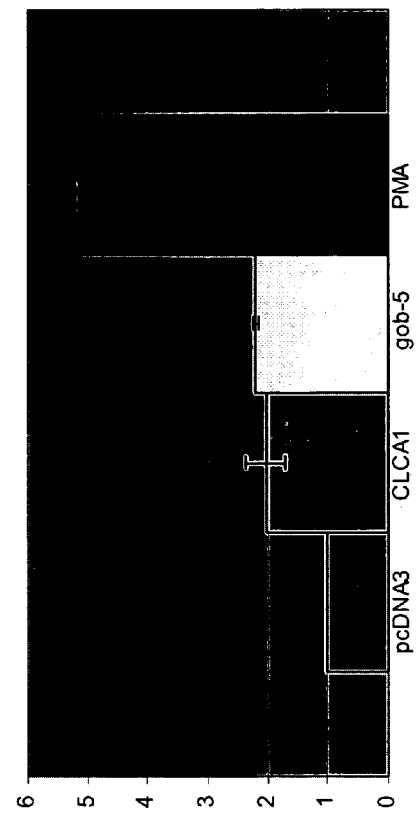
FIG. 12b shows a similar result in HEK293 cells.

The results demonstrated that CLCA1 and gob-5 both induced a two fold increase in gene transcription compared to a negative control (empty plasmid) (FIG. 12a A549 cells and 12b Hek293 cells).

Example 16

Measurement of Whole Cell Chloride Current Induction using Physiological Ca Levels A549 cells and HEK293 cells were each transfected with a plasmid encoding green fluorescent protein and either CLCA1 or gob-5. Individual cells fluorescing green were selected for electrophysiological measurements to determine if CLCA1 and Gob-5, in the presence of physiological levels of calcium, could establish a whole cell chloride current.

All electrophysiological experiments were performed using an AxoPatch200B amplifier (Axon Instruments, Foster City, Calif.). Voltage-clamp protocols and data acquisition were controlled by pClamp8 software (Axon Instruments). Analog data were filtered at 1 KHz and then digitized at 10 kHz with digitizer DIGIDATA 1321A (Axon Instruments, Union City, Calif.). All experiments were performed at room temperature.

Whole-cell Cl-currents across the plasma membrane were isolated pharmacologically by replacing all monovalent cations with cesium. For conventional whole-cell recording through ruptured membrane patches, the bath solution contained: 145 mM CsCl, 2 mM MgCl2, 1 mM $CaCl_2$, 13 mM glucose, and 10 mM Hepes pH 7.4. The pipette solution contained: 145 mM CsCl, 1 mM $MgCl_2$, 1 mM MgATP, 2 mM BAPTA (or 1 mM Dibromo-BAPTA for 1 μM free $Ca^{2+}$), 10 mM Hepes pH 7.2, and an appropriate concentration of $CaCl_2$ (estimated using MaxChelator software, Stanford University, Palo Alto, Calif.) to give a free $[Ca^{2+}]$ between 0.1 and 1 μM.

The whole-cell Cl-currents were monitored with a protocol which began by voltage clamping the cell at 0 mV for 30 milliseconds (ms). Then, the voltage was switched to −100 mV for 200 ms, stepped back to 0 mV for 30 ms, then stepped to 100 mV for 200 ms, and finally stepped back to 0 mV. This sequence of voltage steps was repeated every 5 seconds for 5 minutes to monitor current development. I/V relationship of $Ca^{2+}$ activated whole-cell Cl— current was obtained with the following protocol: membrane potential was held at 0 mV and then 0 stepped to a 300 ms test pulse ranging from −100 mV to +100 mV (in increments of 20 mV) before stepping back to 0 mV. All reported current was measured at 5 ms before the end of test pulse and normalized by cell capacitance. The results presented in FIG. 13a showed that hCLCA1 and gob-5 overexpression in HEK293 and A549 cells does not result in a whole cell chloride current under physiological levels of calcium. Moreover, no dose response in current density to increasing concentrations of calcium was seen (FIG. 13b).

All references cited herein are incorporated herein by reference in their entirety and for all purposes to the same extent as if each individual publication or patent or patent application was specifically and individually indicated to be incorporated by reference in its entirety for all purposes. To the extent publications and patents or patent applications incorporated by reference contradict the disclosure contained in the specification, the specification is intended to supercede and/or take precedence over any such contradictory material.

All numbers expressing quantities of ingredients, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Many modifications and variations of this invention can be made without departing from its spirit and scope, as will be apparent to those skilled in the art. The specific embodiments described herein are offered by way of example only and are not meant to be limiting in any way. It is intended that the specification and examples be considered as exemplary only, with the true scope and spirit of the invention being indicated by the following claims.

What is claimed is:

1. A method of treating a subject having a disease or condition characterized by high levels of mucin, wherein CLCA1 expression or activity is elevated in the subject compared to an individual without the disease or condition, said method comprising administering to said subject a therapeutically effective amount of at least one antibody or antigen binding fragment thereof which binds to CLCA1, wherein the CLCA1 comprises SEQ ID NO: 10, and inhibits or prevents soluble CLCA1 association with a cell membrane molecule, thereby treating the disease or condition.

2. The method of claim 1, further comprising administering a therapeutically effective amount of a second agent, wherein said second agent is an agent known to effectively treat the disease or condition and wherein said second agent does not inhibit or prevent soluble CLCA1 association with a cell membrane.

3. The method of claim 1 or 2, wherein the disease or condition is asthma.

4. The method of claim 1 or 2, wherein the disease or condition is chronic obstructive pathway disease.

* * * * *